United States Patent [19]

Tsai

[11] 4,132,830
[45] Jan. 2, 1979

[54] NOBLE-METAL DENTAL ALLOY AND DENTAL METHOD

[75] Inventor: Min H. Tsai, Van Nuys, Calif.

[73] Assignee: Unitek Corporation, Monrovia, Calif.

[21] Appl. No.: 864,718

[22] Filed: Dec. 27, 1977

Related U.S. Application Data

[63] Continuation-in-part of Ser. No. 765,368, Feb. 2, 1977, abandoned.

[51] Int. Cl.² ............................ A61C 11/00; C22C 5/02
[52] U.S. Cl. ............................................ 428/450; 32/8; 75/165; 427/2
[58] Field of Search ............... 75/165, 172; 32/5, 8, 32/12; 428/433, 434, 469, 470, 471, 472, 450; 427/2

[56] References Cited

U.S. PATENT DOCUMENTS

| 2,781,579 | 2/1957 | Liebig | 32/5 |
| 3,413,723 | 12/1968 | Wagner et al. | 75/165 |
| 3,716,356 | 2/1973 | Burnett | 75/165 |
| 4,053,308 | 10/1977 | Tesk et al. | 148/32 |
| 4,062,676 | 12/1977 | Knosp | 75/165 |

FOREIGN PATENT DOCUMENTS

| 671633 | 1/1939 | Fed. Rep. of Germany | 75/165 |
| 691061 | 4/1940 | Fed. Rep. of Germany | 75/165 |
| 2518355 | 11/1975 | Fed. Rep. of Germany | 32/8 |

Primary Examiner—R. Dean
Assistant Examiner—Michael L. Lewis
Attorney, Agent, or Firm—Christie, Parker & Hale

[57] ABSTRACT

A gold alloy for use in a dental restoration, and which maintains a true yellow-gold color after being cast and having a porcelain jacket fired thereon. The alloy is 83–87% gold, 7–12% platinum, 1.5–3.0% rhodium, and less than 1.0% copper. Other elements are included for grain refining, strength, formation of bonding oxide for the ceramic jacket, and the like.

8 Claims, No Drawings

NOBLE-METAL DENTAL ALLOY AND DENTAL METHOD

CROSS-REFERENCE TO RELATED APPLICATION

This is a continuation-in-part of U.S. patent application Ser. No. 765,368 filed Feb. 3, 1977, and now abandoned.

BACKGROUND OF THE INVENTION

Noble-metal alloys adapted for ceramic bonding (the application of a porcelain jacket or covering) are well known in dentistry, and are used in the manufacture of crowns, bridges, and other prosthetic appliances and restorations used to replace damaged or missing teeth. These so-called "ceramic alloys" typically include about 80–90% gold and relatively high amounts of platinum (5–15%) and palladium (1–10%). Alloys of this type, and application of the alloys in dentistry, are discussed in detail in U.S. Pat. No. 3,413,723—Wagner and Pralow issued Dec. 3, 1968, and for brevity, the disclosure of this patent is incorporated herein by reference.

A problem with known alloys is that they tend to present a somewhat silvery or white-gold appearance, whereas an ideal ceramic alloy should have a true yellow-gold color which remains stable after casting and through repeated firing cycles needed during the application of opaque and porcelain materials. The yellow-gold color is especially desired to match the color of adjacent gold crowns, and because most patients consider this color to be more esthetically and cosmetically pleasing.

I have found that the inclusion of about 1.5% to 3.0% rhodium in the alloy provides a surprisingly true and stable yellow-gold color. Small amounts of rhodium (less than 0.5%) have been previously used for alloy grain-refining purposes, but these quantities of the element are insufficient to produce a stable gold color. Another important factor is to limit copper content of the alloy to under 1.0%. Excessive copper has been found to produce severe oxidation when the alloy is cast, and to adversely affect bonding and color of the porcelain.

SUMMARY OF THE INVENTION

Briefly stated, this invention relates to a castable dental alloy suitable for bonding with dental porcelains, and having a stable yellow-gold color. The alloy includes 83–87% gold, 7–12% platinum, 1.5–3.0% rhodium, up to 1.0% copper (the ratio of rhodium to copper preferably being in the range of 3 to 15), and further elements for grain refining and formation of bonding oxides. A presently preferred formulation of the alloy consists essentially of 85.5% gold, 9.5% platinum, 2.0% rhodium, 0.5% copper, 1.3% silver, 0.5% indium, 0.5% tin, and 0.2% iridium. In method terms, the invention contemplates the technique of making a dental restoration by firing a porcelain jacket over a portion of a cast body of an alloy having the aforesaid characteristics.

DESCRIPTION OF THE PREFERRED EMBODIMENT

The gold-colored ceramic alloy of this invention has the following elemental components (percentages are by weight):

| Element | Preferred Formulation (%) | Acceptable Range (%) |
|---|---|---|
| Gold | 85.5 | 83–87 |
| Platinum | 9.5 | 7–12 |
| Rhodium | 2.0 | 1.5–3 |
| Copper | 0.5 | Less than 1.0 |
| Silver | 1.3 | Less than 4.0 |
| Indium | 0.5 | Less than 2.0 |
| Tin | 0.5 | Less than 1.5 |
| Iridium | 0.2 | Less than 1.0 |
| Iron | | Less than 0.5 |
| Ruthenium | | Less than 1.0 |
| Rhenium | | Less than 1.0 |

This alloy has a melting point in the range of about 1100° C., and has bonding properties and a thermal-expansion coefficient (about $15 \times 10^{-6}$ per ° C.) which are well matched to porcelain jacket materials of the type specified in the aforementioned U.S. Pat. No. 3,413,723. The alloy has been tested and proved satisfactory with dental porcelain available from Vita Zahnfabrik under the trademark VMK-68. Other compatible porcelain materials are available from Dentsply International, Inc. (under the trademark "Biobond") and from the Ceramco Division of Johnson & Johnson.

A cast body of the preferred alloy exhibited an ultimate tensile strength of 52,000 psi, yield strength (0.2% offset) of 39,000 psi, elongation of 12%, Vickers hardness of 140, and bond strength of 12,000 psi. Strength and elongation were measured with an Instron tensile instrument, and Vickers hardness is determined by a microhardness tester with a diamond indenter. Porcelain bond strength to the cast alloy body was tested by the Shell and Nielson technique described at 41 Journal of Dental Research 1424-37 (1962).

The preferred alloy has a rich yellow-gold color after being cast, and this coloration is stable and retained through repeated cycles of firing porcelain layers on the cast alloy body. The alloy further has the highly desirable characteristic that oxides formed during the repeated porcelain firings do not discolor the porcelain jacket. The resulting restoration thus has porcelain surfaces which can be controlled in appearance to match adjacent teeth, and exposed alloy surfaces with a true gold color to match gold crowns or other gold restorations in the patient's mouth.

Platinum is used in the alloy to provide increased strength and for melting-point control. Platinum also contributes to the alloy color, but excessive amounts of this metal provide an overly silver cast to the alloy. Copper also contributes to strength and color control of the alloy, but must be limited in quantity to avoid severe oxidation. Preferably, the ratio of rhodium to copper is held within a range of about 3 to 15.

A relatively high rhodium content as shown above is believed to be the dominant factor in providing a true yellow-gold color which remains stable through repeated porcelain firing cycles. Relatively high amounts (up to 5%) of palladium as used in prior-art alloys are avoided in the new alloy to avoid a silver color in the cast restoration.

Indium and tin are included in the alloy to insure formation of bonding oxides needed for proper adherence of porcelain materials. The primary function of iridium, ruthenium and rhenium is grain refining, and iron (if used) contributes to alloy hardness and strength. The preferred percentage of rhodium (2%) provides good color and good color stability, and higher percentages are normally not needed in view of the relatively high cost of this element.

In use, the alloy is cast into a body shape for the desired prosthetic appliance using conventional investment-casting techniques. Porcelain layers (normally including one or more opaque layers) are then baked on the cast alloy body using well-known porcelain firing methods. The outstanding characteristic of the alloy is maintenance of an attractive and stable yellow-gold color through these firing cycles while retaining the desirable structural and bonding properties of prior-art ceramic alloys.

A number of different alloys were tested in arriving at the preferred formulation and acceptable component ranges. Typical examples of these alloys are set forth below (the components being designated in percentage by weight):

|  | Example 1 | Example 2 | Example 3 | Example 4 |
|---|---|---|---|---|
| Gold | 85.5 | 85.0 | 82.0 | 82.0 |
| Platinum | 9.7 | 8.8 | 12.0 | 12.0 |
| Rhodium | 1.5 | 2.2 | 3.0 | 1.0 |
| Copper | 0.3 | 1.5 | 1.0 | 3.0 |
| Silver | 1.3 | 1.3 | 1.3 | 1.3 |
| Indium | 1.0 | 0.5 | 0.3 | 0.3 |
| Tin | 0.5 | 0.5 | 0.3 | 0.3 |
| Iridium | 0.2 | 0.2 | 0.1 | 0.1 |

The alloy of Example 1 was formulated with rhodium at about the lower end of the acceptable range. This alloy had a beautiful yellow-gold color after being cast, but was only marginally acceptable from the standpoint of color stability after repeated porcelain firing cycles. Oxides of the alloy produced during the firing cycles did not tend to discolor the porcelain jacket.

The alloy of Example 2 was intentionally formulated with excessive copper, and was found to discolor the porcelain jacket. The alloy did, however, exhibit good initial color after being cast, and the color was stable through repeated firing cycles.

The alloys of Examples 3 and 4 were also unsatisfactory in that oxides of both formulations produced discoloration of the porcelain jackets. Example 3 had a good yellow-gold initial color after casting, but the color faded during the porcelain firings. Example 4 showed a silver hue in a gold background after casting, the color fading to white-gold after firing of the porcelain layers. Both Examples 3 and 4 are excessively low in gold content, and Example 4 is low in rhodium and high in copper.

I claim:

1. A castable dental alloy suitable for bonding with dental porcelain and having a stable yellow-gold color which is retained after porcelain is fired on the cast alloy, comprising about 83-87 gold, 7-12% platinum, 1.5-3% Rhodium, less than about 1.0% copper, the ratio of rhodium to copper in the alloy being in the range of 3 to 15, and further elements for grain refining and formation of bonding oxides.

2. A castable dental alloy suitable for bonding with dental porcelain and having a stable yellow-gold color which is retained after porcelain is fired on the cast alloy, consisting essentially of:
   Gold — 83 to 87 percent,
   Platinum — 7 to 12 percent,
   Rhodium — 1.5 to 3 percent,
   Copper — Less than 1 percent,
   Silver — Less than 4 percent,
   Indium — Less than 2 percent,
   Tin — Less than 1.5 percent,
   Iridium — Less than 1 percent,
   Iron — Less than 0.5 percent,
   Ruthenium — Less than 1 percent,
   Rhenium — Less than 1 percent,
   the ratio of rhodium to copper in the alloy being in a range of 3 to 15.

3. The alloy defined in claim 2 formed as a cast body for intra-oral installation, and further comprising a porcelain jacket fired on the body.

4. The alloy defined in claim 2 wherein the constituent elements consist essentially of:
   Gold — 85.5 percent,
   Platinum — 9.5 percent,
   Rhodium — 2.0 percent,
   Copper — 0.5 percent,
   Silver — 1.3 percent,
   Indium — 0.5 percent,
   Tin — 0.5 percent,
   Iridium — 0.2 percent.

5. The alloy of claim 4 formed as a cast body for intra-oral installation, and further comprising a porcelain jacket fired on the body.

6. A method for making a dental restoration, comprising firing of a porcelain jacket on an alloy which includes 83-87% gold, 7-12% platinum, 1.5-3% rhodium, less than 1% copper, the ratio of rhodium to copper being in the range of 3 to 15, and further elements for grain refining and formation of bonding oxides.

7. The method defined in claim 6 wherein the alloy consists essentially of:
   Gold — 83 to 87 percent,
   Platinum — 7 to 12 percent,
   Rhodium — 1.5 to 3 percent,
   Copper — Less than 1 percent,
   Silver — Less than 4 percent,
   Indium — Less than 2 percent,
   Tin — Less than 1.5 percent,
   Iridium — Less than 1 percent,
   Iron — Less than 0.5 percent,
   Ruthenium — Less than 1 percent,
   Rhenium — Less than 1 percent.

8. The method defined in claim 6 wherein the alloy consists essentially of:
   Gold — 85.5 percent,
   Platinum — 9.5 percent,
   Rhodium — 2.0 percent,
   Copper — 0.5 percent,
   Silver — 1.3 percent,
   Indium — 0.5 percent,
   Tin — 0.5 percent,
   Iridium — 0.2 percent.